US00PP17442P2

(12) United States Plant Patent
Bradford

(10) Patent No.: US PP17,442 P2
(45) Date of Patent: Feb. 27, 2007

(54) NECTARINE TREE NAMED 'SUGAR PEARL'

(50) Latin Name: *Prunus persica*
Varietal Denomination: Sugar Pearl

(76) Inventor: Lowell Glen Bradford, 10237 E. Mariposa Way, Le Grand, CA (US) 95333

( * ) Notice: Subject to any disclaimer, the term of this patent is extended or adjusted under 35 U.S.C. 154(b) by 128 days.

(21) Appl. No.: 11/311,173

(22) Filed: Dec. 20, 2005

(51) Int. Cl.
*A01H 5/00* (2006.01)

(52) U.S. Cl. ..... Plt./188
(58) Field of Classification Search ..... Plt./188
See application file for complete search history.

(56) References Cited

U.S. PATENT DOCUMENTS

PP7,049 P 10/1989 Bradford

PP9,960 P 7/1997 Bradford

OTHER PUBLICATIONS

UPOV ROM 2005/05 search for cultivar Summer Pearl.*

* cited by examiner

*Primary Examiner*—Anne Marie Grunberg
*Assistant Examiner*—Annette H Para

(57) ABSTRACT

The present invention relates to a nectarine tree and more particularly to a new and distinct variety broadly characterized by a medium size, vigorous, hardy, self-fertile, productive and regular bearing tree. The fruit matures under the ecological conditions described in mid July, with first picking on Jul. 7, 2005. The fruit is uniformly large in size, excellent in flavor, globose in shape, clingstone in type, very firm in texture, white in flesh color, and full red in skin color. The variety was developed as a first generation cross using 'Summer Bright' (U.S. Plant Pat. No. 7,049) yellow flesh nectarine as the selected seed parent and an unnamed white nectarine (unpatented) as the selected pollen parent.

1 Drawing Sheet

Botanical classification: *Prunus persica.*
Variety denomination: 'SUGAR PEARL'.

BACKGROUND OF THE VARIETY

In a continuing effort to improve the quality of shipping fruits, I, the inventor, typically hybridize a large number of peach, nectarine, plum, apricot, and cherry seedlings each year. I also grow a lesser number of open pollinated seeds of each of these fruits, usually to capture recessive traits. The present invention relates to a new and distinct variety of nectarine tree, which has been denominated varietally as 'SUGAR PEARL'. The present variety was hybridized by me in 1992, grown as a seedling on its own root in my greenhouse, and transplanted to a cultivated area of my experimental orchard at Bradford Farms near Le Grand, Calif., in Merced County (San Joaquin Valley).

The variety was developed as a first generation cross using 'Summer Bright' (U.S. Plant Pat. No. 7,049) yellow flesh nectarine as the selected seed parent and an unnamed white nectarine (unpatented) as the selected pollen parent. A single tree from the stated cross was selected as the claimed variety. Subsequent to origination of the present variety of nectarine tree, I asexually reproduced it by budding and grafting in the experimental orchard described above, and such reproduction of plant and fruit characteristics were true to the original plant in all respects. The reproduction of the variety included the use of 'Nemaguard' (unpatented) rootstock upon which the present variety was compatible and true to type.

The present variety is very distinguished from its seed parent, 'Summer Bright' (U.S. Plant Pat. No. 7,049)

nectarine, by producing nectarines that are white instead of yellow in flesh color and that are sub-acidic instead of acidic in flavor.

The present variety is most similar to 'Grand Pearl' (U.S. Plant Pat. No. 9,960) nectarine tree by producing nectarines that are clingstone in type, globose in shape, full red in skin color, white in flesh color, very firm in texture, and sub-acidic and sweet in flavor, but is distinguished therefrom by being much more productive, by having a small non-showy blossom instead of a large showy blossom, and by producing nectarines that are much less susceptible to skin cracking and russet, that are somewhat larger in size, and that have longer storage capabilities in cold storage.

SUMMARY OF VARIETY

In summary, the present variety is characterized by a medium size, vigorous, hardy, self-fertile, productive and regular bearing tree. The fruit matures under the ecological conditions described in mid July, with first picking on Jul. 7, 2005. The fruit is uniformly large in size, excellent in flavor, globose in shape, clingstone in type, very firm in texture, white in flesh color, and full red in skin color.

DRAWING

The accompanying photograph exhibits four whole fruits positioned to display the characteristics of the skin color and form, one fruit divided transversely to the suture plane to reveal the flesh and stone, and typical leaves.

POMOLOGICAL CHARACTERISTICS

Referring now more specifically to the pomological characteristics of this new and distinct variety of nectarine tree, the following has been observed under the ecological conditions prevailing near Le Grand, Merced County (San Joaquin Valley), Calif., and was developed at the state of firm ripe on Jul. 10, 2005, on the original tree during its thirteenth growing season. All major color code designations are by reference to the Inter-Society Color Council, National Bureau of Standards. Common color names are also used occasionally.

Tree

Size: Medium, reaching and maintaining a height of 11' [3.4 m.] and a spread of 10' [3.1 m.] after thirteen growing seasons utilizing typical dormant pruning.

Vigor: Medium, responding typically to irrigation and fertilization. The variety grows about 3' [0.91 m.] of surplus top-growth during the spring and summer. The plant should be grown on a standard commercial rootstock for production purposes.

Growth: Spreading and dense.

Form: Vase formed.

Hardiness: Hardy with respect to central California winters.

Heat tolerance: Observed to perform adequately in typical central California climatic conditions, which typically include extended periods of heat.

Drought tolerance: Variety is developed for commercial orchards and requires regular irrigation.

Production: Very productive.

Fertility: Self-fertile.

Bearing: Regular bearer with no alternate bearing yet observed.

Approximate chilling requirement: 650 hours.

Trunk:

*Size.*—Medium, with a maximum diameter of 8" [203 mm.] after the thirteenth growing season.

*Texture.*—Shaggy.

*Bark color.*—Grayish yellowish brown [80. gy.yBr].

*Lenticels.*—Approximate Number Per Square Inch: 10. Color: Strong orange yellow [68. s.OY]. Average Size: 3/16" [4.8 mm.] to 7/16" [11.1 mm.]. Shape: Eye-shaped to elongated.

Branches:

*Size.*—Diameter of limb is 4⅜" [111 mm.] measured 12" above the crotch, 2¾" [70 mm.] measured 12" above first fork.

*Texture.*—Medium on first year wood, increasing roughness with age.

*Color.*—1st Year Wood Topside: Dark red [16. d.R.]. 1st Year Wood Underside: Brilliant yellow green [116. brill.YG]. Older Wood: Deep yellowish brown [75. deep yBr].

*Lenticels.*—Approximate Number Per Square Inch: 40. Color: Light orange yellow [70 l.OY]. Typical size: 1/16" [1.6 mm.] to 3/16" [4.8 mm.]. Shape: Eye-shaped to elongated.

Leaves:

*Size.*—Large. Average Length: 6¼" [159 mm.]. Average width: 1 1/34" [44.5 mm.].

*Arrangement.*—Alternate.

*Thickness.*—Medium.

*Form.*—Elliptical.

*Apex.*—Acuminate.

*Base.*—Acute.

*Surface.*—Smooth.

*Color.*—Dorsal Surface: Moderate olive green [125. m.OlG]. Ventral Surface: Moderate yellow green [120 m.YG].

*Margin.*—Finely serrate.

*Venation.*—Pinnately net veined.

*Vein color.*—Light yellow green [119. l.YG].

*Petiole.*—Average Length: ½" [12.7 mm.]. Average Thickness: ¼" [6.4 mm.]. Color: Light yellow green [119. l.YG].

*Stipules.*—Number: 2 per bud, 6 per growing tip. Average Length: ⅜" [9.5 mm.]. Color: Brilliant yellow green [116. brill.YG].

*Glands.*—Number: Usually 2 or 4. Position: Alternately positioned on the petiole and base of blade. Size: Large. Form: Reniform. Color: Light yellow green [119. l.YG] when young.

*Leaf buds.*—Pointed.

Flower buds:

*Hardiness.*—Hardy, with respect to central California winters.

*Diameter.*—Typically ¼" [6.4 mm.] 1 week before bloom.

*Length.*—Typically ⅜" [9.5 mm.] 1 week before bloom.

*Form.*—Not appressed.

*Surface.*—Pubescent.

*Color.*—Moderate purplish red [258. m.pR].

Flowers: Perfect, complete, perigynous, usually a single pistil, typically 24–28 or more stamens, five sepals and petal locations alternately positioned.

*Type.*—Small.

*Average flower diameter.*—1⅛" [28.6 mm.].

*Number of petals.*—Five, no double blossom observed.

*Petal shape.*—Oval.

*Petal margin.*—Wavy.

*Average petal diameter.*—⅜" [9.5 mm.].

*Average petal length.*—9/16" [14.3 mm.].

*Petal apex.*—Rounded.

*Petal base.*—Cuneate to obtuse.

*Petal color.*—Light purplish pink [249. l.pPk] toward the center with Moderate purplish red [258. m.pR] toward the margin.

*Anther color.*—Deep reddish orange [36. deep rO] over a Brilliant orange yellow [67. brill.OY] center.

*Stigma color.*—Light greenish yellow [101. l.gY].

*Sepal color.*—Dark purplish red [259. d.pR].

*Sepal length.*—¼" [6.4 mm.].

*Sepal width.*—3/16" [4.8 mm.].

*Average pistil length.*—½" [12.7 mm.].

*Average stamen length.*—7/16" [11.1 mm.].

*Fragrance.*—Moderate.

*Blooming period.*—Medium compared to other varieties.

*Onset of bloom.*—One percent on Feb. 22, 2005.

*Date of full bloom.*—Mar. 2, 2005.

*Duration of bloom.*—One to two weeks, dependent on ambient temperature.

*Number per cluster.*—1 to 2 with single flowers most common.

FRUIT

Maturity when described: Firm ripe, Jul. 10, 2005.

Date of first picking: Jul. 7, 2005.

Date of last picking: Jul. 20, 2005.

Size: Uniform, large.

*Average diameter axially.*—2⅞" [73.0 mm.].

*Average diameter across suture plane.*—2⅞" [73.0 mm.].

*Typical weight.*—7.0 ounces [198 grams].

Form: Symmetrical, uniform.
*Longitudinal section form.*—Circular.
*Transverse section through diameter.*—Circular.
Suture: An inconspicuous line on side, shallow groove toward apex, extends from base to slightly beyond apex, with slight depression at the pistil point.
Ventral surface: Rounded, lipped throughout but stronger toward the apex.
Lips: Slightly unequal on the side, equal toward the apex.
Cavity: Flaring, elongated in suture plane, suture showing on both sides, Yellowish white [92. yWhite] stem markings typical.
*Depth.*—½" [12.7 mm.].
*Breadth.*—⅞" [22.2 mm.].
Base: Somewhat truncate, cordate if viewed parallel to the suture.
Apex: Rounded.
Pistil point: Apical, negligible in length, depressed within the suture.
Stem: Medium.
*Average length.*—⅜" [9.5 mm.].
*Average width.*—3/16" [4.8 mm.].
Skin:
*Thickness.*—Medium.
*Surface.*—Smooth, resistant to russet during a wet season.
*Tenacity.*—Tenacious to flesh.
*Astringency.*—Nonastringent.
*Tendency to crack.*—None observed.
*Color.*—Very deep red [14. v.deep R] smoothly blending to Moderate red [15. m.R] with some Dark orange yellow [72. d.OY] freckling toward the apex.
Flesh:
*Color.*—Yellowish white [92. yWhite] to stone with very little Moderate red [15. m.R] streaking close to the stone.
*Amygdalin.*—Wanting.
*Juice.*—Moderate, rich.
*Texture.*—Very firm, crisp.
*Fibers.*—Abundant, fine, and tender.
*Ripens.*—Slightly earlier toward the apex and along cheeks.
*Flavor.*—Sub-acid and sweet, with an average of 18 brix.
*Aroma.*—Very slight.
*Eating quality.*—Excellent.

STONE

Type: Clingstone.
Form: Oval.
Hilum: Narrow.
Base: Straight.
Apex: Acute, with an average angle of 75 degrees.
Sides: Slightly unequal.
Surface: Irregularly to horizontally furrowed toward the apex, pitted toward the base.
Ridges: Jagged.
External color of stone: Moderate brown [58. m.Br] when dry.
Surface color of stone cavity: Light yellowish brown [76. l.yBr].
Average pit wall thickness: ¼" [6.4 mm.].
Average width: 1⅛" [28.6 mm.].
Average length: 1 9/16" [39.7 mm.].
Average breadth: ⅞" [22.2 mm.].
Tendency to split: Very slight.
Kernel:
*Form.*—Oval.
*Skin color.*—Moderate orange yellow [71. m.OY].
*Pellicle color.*—Dark yellowish brown [78. d.yBr].
*Vein color.*—Moderate brown [58. m.Br].
*Taste.*—Bitter.
*Viable.*—Yes.
*Average width.*—½" [12.7 mm.].
*Average length.*—11/16" [17.5 mm.].
*Amygdalin.*—Abundant.

USE

Market: Fresh market and long distance shipping.
Keeping quality: Excellent. Fruit quality observed to remain in good condition with no internal browning after 30 days in standard cold room at 36° Fahrenheit [2° Celsius].
Shipping quality: Good.
Resistance to insects: No unusual susceptibilities noted.
Resistance to diseases: No unusual susceptibilities noted.

Other Notes

Although the new variety of nectarine tree possesses the described characteristics under the ecological conditions at Le Grand, Calif., in the central part of the San Joaquin Valley, it is to be expected that variations in these characteristics may occur when farmed in areas with different climatic conditions, different soil types, and/or varying cultural practices.

I claim:

1. A new and distinct variety of nectarine tree named 'SUGAR PEARL', substantially as illustrated and described, that is most similar to 'Grand Pearl' (U.S. Plant Pat. No. 9,960) nectarine tree by producing nectarines that are clingstone in type, globose in shape, full red in skin color, white in flesh color, very firm in texture, and sub-acidic and sweet in flavor, but is distinguished therefrom by being much more productive, by having a small non-showy blossom instead of a large showy blossom, and by producing nectarines that are much less susceptible to skin cracking and russet, that are somewhat larger in size, and that have longer storage capabilities in cold storage.

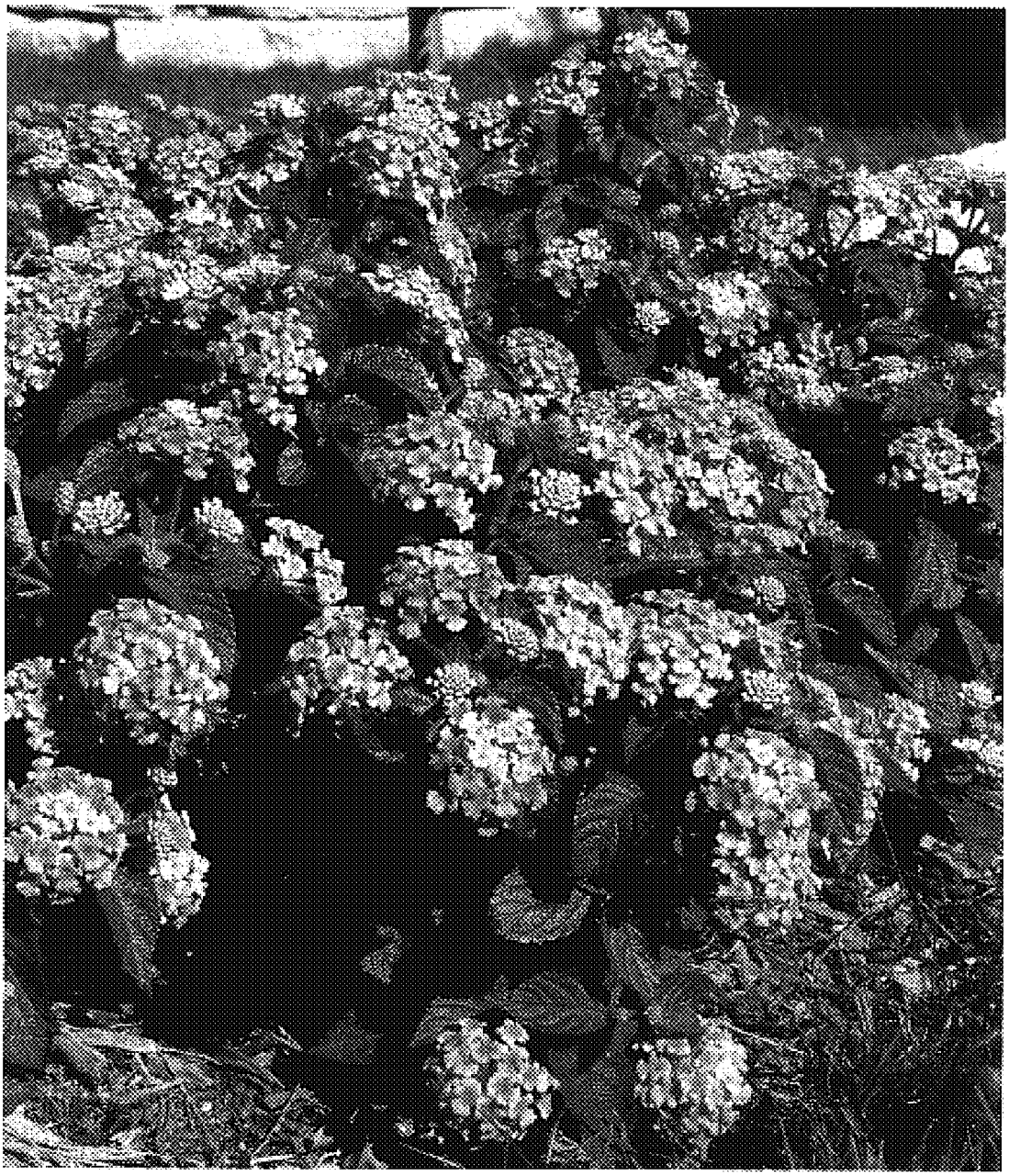

* * * * *